(12) United States Patent
Vohra et al.

(10) Patent No.: US 6,740,253 B2
(45) Date of Patent: May 25, 2004

(54) PREPARATION OF NON-HAZARDOUS BROMINATING REAGENTS

(75) Inventors: Rajinder Nath Vohra, Bhavnagar (IN); Pushpito Kumar Ghosh, Bhavnagar (IN); Maheshkumar Ramniklal Gandhi, Bhavnagar (IN); Himanshu Labhshanker Joshi, Bhavnagar (IN); Hasina Hajibhai Deraiya, Bhavnagar (IN); Rohit Harshadray Dave, Bhavnagar (IN); Koushik Halder, Bhavnagar (IN); Kishorkumar Manmohandas Majeethia, Bhavnagar (IN); Sohan Lal Daga, Bhavnagar (IN); Vadakke Puthoor Mohandas, Bhavnagar (IN); Rahul Jasvantrai Sanghavi, Bhavnagar (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/055,814

(22) Filed: Jan. 23, 2002

(65) Prior Publication Data

US 2003/0136941 A1 Jul. 24, 2003

(51) Int. Cl.$^7$ ............... C09K 3/00; C07C 19/075

(52) U.S. Cl. ............ 252/182.16; 106/287.27; 564/218; 568/726; 568/776; 568/779; 570/235; 570/246; 570/261

(58) Field of Search ............ 106/287.27; 564/218; 568/726, 776, 779; 570/246, 261, 233; 252/182.16

(56) References Cited

U.S. PATENT DOCUMENTS 6,365,786 B1 * 4/2002 Ramachandraiah et al. . 568/726

* cited by examiner

*Primary Examiner*—Brian Davis
(74) *Attorney, Agent, or Firm*—Ladas & Parry

(57) ABSTRACT

The present invention relates to a non-hazardous brominating reagent from an aqueous alkaline bromine byproduct solution obtained from bromine recovery plant and containing 25 to 35% bromine dissolved in aqueous lime or sodium hydroxide containing alkali bromide and alkali bromate mixture having bromide to bromate stoichiometric ratio in the range of 5:1 to 5.1:1 or 2:1 to 2.1:1 and a pH ranging between 8–12 and also relates to a method for borminating aromatic compounds by using the above brominating agent.

13 Claims, No Drawings

PREPARATION OF NON-HAZARDOUS BROMINATING REAGENTS

FIELD OF THE INVENTION

The present invention relates to the preparation of non-hazardous brominating reagents.

The invention particularly relates to suitable mixtures of alkali bromide and alkali bromate salts that can be prepared in stable form from inexpensive raw material and can be used as a substitute for liquid bromine in aromatic bromination reactions and also bromine addition in unsaturated compounds.

BACKGROUND OF THE INVENTION

Liquid bromine is used to prepare a variety of brominated compounds through addition or substitution reactions. The latter includes commercially important products such as: tetrabromobisphenol-A (TBBPA)—a flame retardant, eosin—a pigment used in personal care products, bromoacetanilide—an analgesic and antipyretic agent, tribromophenol—an intermediate used in the manufacture of antiseptic, germicide, fungicide, fire extinguishing fluids, and fire retardant, and 2-bromo-4-nitro acetanilide—a drug intermediate used in the preparation of nimenslide. Likewise, there are a number of addition compounds of bromine that have utility as intermediates or products. However, liquid bromine is hazardous by nature and requires extreme care in its production, transportation, and utilization. Moreover, for substitution reactions depicted by equation 1, half of the bromine atoms end up in the effluent as hydrobromic acid.

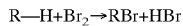

$$R\text{—}H + Br_2 \rightarrow RBr + HBr \quad (1)$$

Bromine atom efficiency of liquid bromine can be 100% for addition across olefins (equation 2) but the need to handle the hazardous liquid bromine remains.

$$R\text{—}CH=CH_2 + Br_2 \rightarrow RCHBrCH_2Br \quad (2)$$

Z. E. Jolles (Bromine and its compounds, Ernest Benn Limited London 1966, p352) describe the preparation of a number of dibromo compounds through addition of liquid bromine across unsaturated organic compounds. Such products are obtained in high yields but an important disadvantage is the hazards of handling liquid bromine.

C. A. Buechler and D. E. Pearson, (Survey of organic syntheses Wiley-Inter science, New York 1970 Chapter7) have reported the preparation of tribromophenol using liquid bromine as brominating agent. The drawbacks of this method are that it requires special devices for handling corrosive liquid bromine and at least half of the bromine atoms in the reagent end up in the effluent in the form of hydrobromic acid.

Reference may be made to S. Armstrong in U.S. Pat. No. 5,475,153, Dec. 12, 1995 who brominated Bisphenol-A with liquid bromine to get 98% pure tetrabromobisphenol-A (m.p, 180° C.) and where hydrogen peroxide was combined with the reactants to reuse the HBr produced as in equation 1 and thereby reduce the amount of bromine required. However, the principal difficulty of the hazardous nature of liquid bromine remains.

Brominating agents that are easy to handle are known but are used mainly for more selective transformations or those where bromine is less effective. A. Groweiss in *Organic Process & Development* 2000, 4, 30–33, described the use of sodium bromate for bromination of aromatic compounds that contain deactivating substituents such as nitrobenzene, benzoic acid, benzaldehyde, 4-nitrofluorobenzene and 4-fluorobenzoic acid. In this process, the addition of a strong acid such as sulfuric acid into a stirred aqueous solution or slurry of the substrate and stoichiometric quantity of bromate salt at 40–100° C., leads to the decomposition of the bromate ions and production of active brominating species. The drawback of sodium bromate is that it is costly and its use cannot be justified in more conventional bromination reactions that can be effected by liquid bromine as such.

Z. E. Jolles (Bromine and its compounds, Ernest Benn Limited London 1966, p394) has added a mixture of 356 g (2 moles) of N-bromosuccinimide and 4 g (0.0165 moles) of benzoyl peroxide over 20 min to a solution of 220 g (2.24 moles) of 3-methyl thiophene and 4 g (0.0165 moles) benzoyl peroxide in 700 ml of dry benzene under stirring at reflux conditions. After all the succinimide is added, the reaction mixture is cooled to below 5° C. The benzene is distilled at 75–78° C. under reduced pressure to give 280 g of 3-bromomethyl-thiophene. Although N-bromosuccinimide is a useful reagent for specific bromination reactions, it is a costly brominating agent and its use cannot be justified in those bromination reactions where liquid bromine would suffice; even more so since its preparation involves use of liquid bromine in any case (N-bromosuccinimide is prepared by reacting succinimide with bromine liquid below 0° C. in potassium hydroxide solution).

P. C. Merker and J. A. Vona (*J Chem. Ed.* 1949, 26, 613) prepared p-bromoacetanilide by reacting 31.5 g (0.232 mole) of acetanilide in 50 ml of glacial acetic acid with 38 g (0.119 mole) of pyridinium bromideperbromide in hot 40 ml glacial acetic acid. The mixture was allowed to stand at room temperature for 30 min. To it, 2 ml of saturated sodium bisulfite solution was added. The resulting mass was filtered, washed with water and finally recrystallized from hot 95% aqueous ethanol to yield 13 g of p-bromoacetanilide having m.p. 168° C. The drawbacks of this method are that the brominating agent requires liquid bromine and hydrobromic acid in its preparation (L. F. Fieser and M. Fieser, *Reagents for Organic Chemistry* Vol. 1, John Wiley, New York, 1967, p967) and the reagent is costlier than liquid bromine.

G. Rothenberg and J. H. Clark (Organic Process & Development 2000, 4, 270–274) have claimed the catalytic bromination of various aromatic compounds using an alkali bromide or hydrobromic acid and hydrogen peroxide in the presence of 1–2 mol % vanadium pentoxide catalyst. The drawbacks of this method are that more than stoichiometric quantities of hydrogen peroxide are required and the reaction needs a catalyst.

G. Ramachandraiah, P. K. Ghosh, A. S. Mehta, R. P. Pandya, A. D. Jethva, S. S. Vaghela, S. N. Misra (pending U.S. pat. appln. Ser. No. 09/767,667 [2001]) have prepared tetrabromobisphenol-A from bisphenol-A using 2:1 molar ratio of bromide and bromate salts as brominating agent. To 0.50 kg (2.19 moles) of bisphenol-A in 1.50 liters of methylene chloride, a solution of 0.63 kg (6.14 moles) of sodium bromide, 0.44 kg (2.93 moles) of sodium bromate and 1 g of sodium lauryl sulfate in 2.5 liters of water was added. The flask was cooled to 10° C. by placing it in a cold water bath. To it, 0.90 liters (10.8 moles) of 12 N hydrochloric acid was added over 3 h under stirring. The contents were stirred for another 0.5 h and the separated solid product was filtered, washed twice with deionized water and dried in oven at 100° C. to give a yield of 0.85 kg of TBBPA. The organic layer was recycled in subsequent batches. The isolated yield of TBBPA (m.p. 178–180° C.) over three batches was 85.4%. Although the method has several advantages in that the brominating reagent is easy to handle, no catalyst is required, the bromine atom efficiency for the aromatic substitution reaction studied is as high as 95–100%, the main drawback of this method is that alkali bromide and bromate salts are individually much costlier than liquid bromine. Moreover the 4:2 stoichiometry of bromide:bromate is suitable for substitution reactions but not for addition of bromine across double bonds.

According to the present invention, the main drawback of U.S. Pat. No. 6,365,786 has been overcome by using a mixture of alkali bromide and alkali bromate salts of the desired ratios that can be prepared inexpensively from the intermediate of bromine recovery plants, the said mixture being easy to handle and stable under storage while, under the conditions of bromination reaction, the bromide and bromate salts self annihilate one another to create reactive species of bromine that are useful in the safe preparation of several organo bromine compounds as demonstrated through working examples.

OBJECTS OF THE INVENTION

The main object of the present invention is the preparation of suitable mixtures of alkali bromide and alkali bromate salts that are easy to handle, stable on storage, and can replace corrosive liquid bromine in bromination reaction.

Another object of the invention is to prepare a non-hazardous brominating reagent from an aqueous alkaline bromine byproduct solution obtained from bromine recovery plant.

Another object of the present invention is to utilize the intermediate of bromine recovery plants that are based on the "Cold Process" which typically contains 25–35% (w/v) "bromine" dissolved in lime or sodium hydroxide.

Yet, another object of the present invention is to alter the composition of the industrial alkaline bromine mixture to maximize bromine atom efficiency in the reactions of equations 1 and 2 and minimize discharge in effluent.

Yet, another object of the present invention is to adjust appropriately the bromide:bromate ratio of the intermediate by adding alkali bromide salt to achieve a precise stoichiometry of 5:1 bromide:bromate suitable for equation 2.

Yet, another object of the present invention is to adjust appropriately the bromide:bromate ratio of the intermediate by adding alkali bromate salt to achieve a stoichiometry of 2:1 bromide:bromate suitable for equation 1.

Yet, another object of the present invention is to adjust appropriately the bromide:bromate ratio of the intermediate by utilizing inexpensive oxidizing agents such as sodium hypochlorite that can oxidize bromide ion to bromate ion to achieve a stoichiometry of 2:1 bromide:bromate suitable for equation 1.

Yet another object of the present invention is to make the brominating reagent in the desired physical form.

Yet another object of the present invention is to activate the brominating agent with a suitable acid during bromination reactions of organic substrates.

SUMMARY OF THE PRESENT INVENTION

Accordingly, the present invention provides an non-hazardous brominating reagent from an aqueous alkaline bromine byproduct solution obtained from bromine recovery plant and containing 25 to 35% bromine dissolved in aqueous lime or sodium hydroxide containing alkali bromide and alkali bromate mixture having bromide to bromate stoichiometric ratio in the range of 5:1 to 5.1:1 or 2:1 to 2.1:1 and a pH ranging between 8–12. This invention also provides a process for producing the above said brominating agent and use of said brominating agent for brominating organic substrate.

DETAILED DESCRIPTION OF THE INVENTION

Accordingly, the present invention provides a stable non-hazardous brominating reagent from an aqueous alkaline bromine byproduct solution obtained from bromine recovery plant, said bromine byproduct solution containing 25 to 35% bromine dissolved in aqueous lime or sodium hydroxide in the form of alkali bromide and alkali bromate mixture, said reagent having a pH ranging between 8.5–10.5 and containing 100–350 g/L bromine or in a solid form having 45–55% (w/w) bromine.

In an embodiment of the invention relates to a cost-effective process for the preparation of a stable and non-hazardous brominating reagent which comprises treating aqueous alkaline bromine containing 25–35% bromine dissolved in aqueous lime or sodium hydroxide as an alkali bromide and alkali bromate mixture at a pH ranging between 8–12 with alkali bromide to increase the stoichiometric ratio of bromide to bromate in the range of 5.1:1 to 5:1 or adding an oxidizing agent to decrease the stoichiometric ratio of bromide to bromate in the range of 2.1:1 to 2:1 to obtain the desired brominating reagent solution having pH ranging between 8.5–10.5 and containing 100–350 g/L bromine, optionally evaporating the above said brominating reagent solution to obtain the desired brominating reagent in a solid form possessing 45–55% (w/w) bromine.

In another embodiment of the invention, wherein the bromide to bromate ratio is increased to 5:1 by adding appropriate quantity of alkali bromide salt to the aqueous alkaline bromine solution.

In still another embodiment of the invention, wherein the bromide to bromate ratio of 2:1 is achieved by treating the aqueous alkaline bromine solution with 1–10% concentration of aqueous sodium hypochloride for a period of 6–24 hours at a temperature in the range of range of 25–30° C. and more preferably by adding alkali into the aqueous alkaline bromine solution followed by passing chlorine gas to generate hypochloride in situ to convert bromide salt to bromate salt by an oxidation process.

Yet another embodiment of the invention, wherein the bromide to bromate ratio of alkaline bromine mixture is decreased by adding appropriate quantity of alkaline bromate salt, preferably sodium or calcium bromate while ensuring that pH of the solution remains between 8–10 and there is no rise in temperature.

Yet another embodiment of the invention, wherein the solution of brominating reagent is evaporated by conventional techniques, preferably in solar pans for large scale production to obtain solid brominating reagent which is finally ground to get a homogenous mixture of salts having bromine content in the range of 90–100%.

Yet another embodiment of the invention, wherein the said brominating reagent is activated in situ during the bromination reaction through addition of stoichiometric quantity of a mineral acid, preferably hydrochloric acid.

One more embodiment of the invention provides a method for brominating aromatic compounds by using brominating reagent as claimed in claim 1, wherein the aromatic compound used is selected from group consisting of bisphenal A, bromophenol and olefin selected from styrene and cyclohexene and other class of aromatic compounds, the said method comprising: treating aqueous alkaline bromine containing 25–35% bromine dissolved in aqueous lime or sodium hydroxide as an alkali bromide and alkali bromate mixture at a pH ranging between 8–12 with alkali bromide to increase the stoichiometric ratio of bromide to bromate in the range of 5.1:1 to 5:1 or adding an oxidizing agent to decrease the stoichiometric ratio of bromide to bromate in the range of 2.1:1 to 2:1 to obtain the desired brominating reagent solution having pH ranging between 8.5–10.5 and containing 100–350 g/L bromine, optionally evaporating the above said brominating reagent solution to obtain the desired brominating reagent in a solid form possessing 45–55% (w/w) bromine with active bromine content that is 90–100% of total bromine content and activating the brominating agent in situ during bromination reaction by adding 9–12 ml of 12N hydrochloric acid into the reaction vessel containing 1–3 g of organic substrate and 1–20 g of said brominating reagent or alternatively by adding 1–20 g of brominating reagent into the reaction vessel containing 1–3 g of organic substrate and 9–12 ml of 12N hydrochloric acid.

The present invention provides a cost-effective process of preparation of a stable and non-hazardous brominating reagent containing 5:1 to 2:1 stoichiometric ratio of alkali bromide:alkali bromate which comprises treatment of aqueous alkaline bromine containing 25–35% bromine dissolved in aqueous lime or sodium hydroxide as an alkali bromide/alkali bromate mixture in the pH range 8–12 with an appropriate quantity of alkali bromide to increase bromide::bromate ratio or with an oxidizing agent to decrease bromide/bromate ratio, as appropriate, yielding the desired brominating reagent solution with pH 8–10 and containing 100–350 g/L bromine, optionally evaporating the solution to yield a solid form of brominating agent possessing 45–55% (w/w) bromine with active bromine content that is 90–100% of total bromine content, and activating the brominating agent in situ during bromination reactions by controlled addition of appropriate quantity of mineral acid into the reaction vessel containing organic substrate and brominating reagent or alternatively through controlled addition of brominating reagent into reaction vessel containing organic substrate and mineral acid.

In an embodiment of the present invention, the alkaline bromine having 29.3% (w/v) bromine dissolved in sodium hydroxide (37.2° Be, pH 8.73) and 28.1% (w/v) bromine dissolved in lime (37.2° Be, pH 10.25) are obtained from bromine recovery plants based on "Cold Process" technology.

In another embodiment of the present invention, alkaline bromine may be obtained from other sources than bromine recovery plants based on "Cold Process" technology.

In yet another embodiment of the present invention bromide salt is added to the alkaline bromine having bromide to bromate ratio less than 5:1 to adjust the bromide to bromate ratio to 5:1.

In yet another embodiment of the present invention, the alkaline bromine is reacted with required quantity of sodium hypochlorite in a closed vessel over a period of 6–24 h to obtain the brominating reagent with 2:1 ratio of bromide to bromate.

In yet another embodiment of the present invention, the alkaline bromine may be mixed with required quantity of a bromate salt over a period of 10–30 min to obtain the brominating reagent with 2:1 stoichiometry of bromide:bromate.

In yet another embodiment of the present invention, the reaction/mixing is conducted typically in the temperature range between 25–30° C.

In yet another embodiment of the present invention, the treated alkaline bromine solutions containing 5:1 and 2:1 bromide to bromate are used as reagents for bromine addition and substitution reactions, respectively.

In yet another embodiment of the present invention, the brominating reagent solution is evaporated and dried to obtain a solid, which can be used as brominating reagent.

In yet another embodiment of the present invention, the brominating agent can be activated during bromination reactions addition of a suitable acid.

In yet another embodiment of the present invention the acid used during the bromination reaction is preferably an inexpensive mineral acid and more specifically an acid which produces soluble calcium salts which is advantageous when the brominating agent is based on alkaline (lime) bromine and/or calcium hypochlorite.

Bromine is manufactured commercially by the "Steaming Out" and "Cold" Processes. In the latter process, bromine liberated from the feed by sparging with chlorine gas is initially trapped in aqueous solution in concentrated form wherein it reacts with the alkali and disproportionate as per the reaction of equation 3 to produce five parts of bromide ion and one part of bromate ion. The medium is then acidified to re-liberate bromine as per the reaction of equation 4. This bromine can then be collected.

$$3Br_2 + 6OH^- \rightarrow 5Br^- + BrO_3^- + 3H_2O \tag{3}$$

$$5Br^- + BrO_3^- + 6H^+ \rightarrow 3Br_2 + 3H_2O \tag{4}$$

whereas, the mixture of bromide and bromate is unstable under acidic conditions, it is stable over many months under alkaline conditions. It has been found in the course of this invention that it is possible to apply the knowledge of equation 4 and convert the product mixture of equation 3 into a reagent to carry out the reaction of equation 2 as shown below:

$$5Br^- + BrO_3^- + 6H^+ \rightarrow [3Br_2] + 3H_2O \tag{5a}$$

$$R-CH=CH_2 + [Br_2] \rightarrow RCHBrCH_2Br \tag{equation 2}$$

Care must, however, be taken to ensure that sufficient time is given for equation 5a so that molecular bromine can be generated prior to the reaction of equation 2. Otherwise, tendency to form side products is higher as demonstrated later in the examples.

The reagent can also be used to carry out equation 6, as described in pending U.S. pat. appln. Ser. No. 09/767,667 (2001), when the reaction mixture containing such brominating reagent and organic compound is acidified whereupon active bromine is generated. Alternatively, the brominating agent can be added into a solution of the organic compound and desired quantity of acid.

$$3R-H + 5Br^- + BrO_3^- + 6H^+ \rightarrow 3RBr + 3HBr + 3H_2O \tag{6}$$

Pending U.S. pat. appln. Ser. No. 09/767,667 (2001) states that the bromide/bromate stoichiometric ratio should be 4:2 instead of 5:1 for maximum bromine atom efficiency, as illustrated by equation 7.

$$6R-H + 4Br^- + 2BrO_3^- + 6H^+ \rightarrow 6RBr + 6H_2O \tag{7}$$

It occurred to us in the course of the invention that the desired bromide:bromate stoichiometric ratio can be achieved in cost-effective manner as shown by equations 8 and 9. Hypochlorite is generated as in equation 8 and used in the reaction of equation 9 to attain the desired 4:2 stoichiometry of bromide:bromate.

$$3Cl_2 + 6OH^- \rightarrow 3ClO^- + 3Cl^- + 3H_2O \quad (8)$$

$$5Br^- + BrO_3^- + 3ClO^- \rightarrow 4Br^- + 2BrO_3^- + 3Cl^- \quad (9)$$

The preparation of hypochlorite involves handling alkali and chlorine, both of which are used by manufacturers of bromine by the "Cold Process". Moreover, hypochlorite is among the cheapest oxidizing agents, which can effect the desired oxidation reaction of equation 9, and, therefore, is an ideal choice although other oxidizing agents could also be used.

The reaction of equation 9 is carried out in the laboratory in a stoppered 0.25–5.00 L round bottom flask. Alkaline bromine containing 3–265 g of dissolved bromine in lime or sodium hydroxide was mixed with calculated amount 0.8–63.0 g of sodium hypochlorite under thorough stirring. The reactants were allowed to react for 6–24 h to obtain the desired brominating reagent in solution form. The temperature of the vessel during the reaction was in the range of 27–30° C. It is advisable to conduct the reaction of sodium hypochlorite with alkaline bromine in a closed vessel for at least 12 h.

In the second method, the alkaline bromine containing 3–265 g of dissolved bromine was mixed with a solution of calculated amount (1.5–118 g) of sodium bromate in a 0.25–5.00 L flask to give liquid brominating reagent or solid on evaporation and drying of it under vacuum.

Better brominating reagent for equation 7 is obtained if the bromide:bromate ratio is maintained between 2.0–2.1. Brominating agent with bromide:bromate>2.1 leads to decrease in bromine atom efficiency whereas undesired products tend to be produced when bromide:bromate<2.

In the preferred form of the invention, the aqueous brominating agent with pH in the range 8.5–10.5 and the desired stoichiometry of bromide:bromate was evaporated on a steam bath and dried under vacuum to get the reagent in solid form. Bromine manufacturers generally have access to solar evaporation ponds that can be used to produce the solid reagent cost-effectively on large scale. Apart from the advantage of higher bromine content, such form of the reagent would be easier and cheaper to transport than the solution.

The brominating reagent (solid and solution) was characterized by determining its bromate and bromide contents. 1 g of solid or 1 ml of liquid brominating reagent was dissolved/diluted with water to a volume of 100 ml and used as stock in the estimation of bromate and bromide. To estimate bromide, 1–4 ml of the stock was taken in a 25 ml volumetric flask and 2 ml of 9 M sulfuric acid was added and the solution was diluted up to the 25 ml mark. For bromate estimation, 0.1–0.4 ml of the stock was likewise taken in a 25 ml volumetric flask and into it was added a large excess (1 g) of sodium bromide and 2 ml of 9 M sulfuric acid and the volume made up to the 25 ml mark. The liberated bromine as a result of the reaction between bromide and bromate in presence of acid was estimated spectrophotometrically (K. Kumar and D. W. Margerum *Inorg. Chem.* 1987 26, 2706–2711) by measuring the absorbance at 390 nm and coefficient ($\epsilon$, 167 $M^{-1}$ $cm^{-1}$ in absence and 522 $M^{-1}$ $cm^{-1}$ in the presence of large excess of bromide) values. The homogeneity of solid brominating reagent was confirmed by estimating bromate and bromide composition in 1 g samples drawn from different parts of the sample.

Since the bromide:bromate stoichiometry was always maintained slightly higher than the theoretical ratio of 4:2 as per the requirement of equation 7, the active bromine was always less than 100% and was estimated with the help of equation 10:

$$\{3\times[BrO_3^-]/([BrO_3^-]+[Br^-])\}\times 100\% \quad \text{(equation 10)}$$

The following examples illustrate the method of preparation of the brominating agent and its application in organic bromination reactions.

The important inventive steps involved in the present invention are that (i) the brominating reagent can be prepared from mixed salts of alkali bromide and bromate, either as a solution or solid as desired, (ii) such mixed salt can be prepared cost-effectively from the alkaline bromine intermediate produced in the process of bromine recovery through the "Cold Process", (iii) the ratio of bromide to bromate can be suitably adjusted for aromatic bromination reactions through oxidation with inexpensive hypochlorite which can be prepared, in turn, using chlorine gas and alkali, both of which are used routinely in the "Cold Process", and (iv) the brominating agent can be activated in presence of acid for carrying out organic bromination reactions with high yields and atom efficiency.

One more embodiment of the invention provides a cost effective process for the preparation of a non-hazardous brominating reagent from an aqueous alkaline bromine byproduct solution obtained from bromine recovery plant and containing 25 to 35% bromine dissolved in aqueous lime or sodium hydroxide containing alkali bromide/bromide mixture having a pH range of 8–12.

Another embodiment of the invention, wherein the aqueous alkaline bromine solution with bromide:bromate ratio typically in the range of 4.5:1 to 5.5:1 and preferably in the range of 5:1 to 5.1:1.

In another embodiment of the invention, wherein the aqueous alkaline bromine solution with bromide:bromate ratio typically in the range of 2:1 to 2.1:1.

Still another embodiment of the invention, wherein bromide to bromate ratio is increased to 5:1 to 5.1:1 by adding appropriate quantity of alkali bromide salt to the aqueous alkaline bromine solution.

Yet another embodiment of the invention, wherein bromide to bromate ratio of 2.1:1 to 2:1 is achieved by treating the aqueous alkaline bromine solution with 1–10% concentration of aqueous sodium hypochloride for a period of 6–24 hours at a temperature range of 25–30° C. and more preferably by adding alkali into the aqueous alkaline bromine solution and passing chlorine gas to generate hypochloride in situ which can convert bromide salt to bromate salt by the process of oxidation.

Yet another embodiment of the invention, wherein ratio of bromide to bromate is decreased by addition of appropriate quantities of alkaline bromate salt sodium or calcium bromate maintaining the pH of the final solution between 8–10 and without any rise in temperature of the solution.

Yet another embodiment of the invention, wherein the solution of brominating reagent is evaporated by conventional techniques, preferably in solar pans for large scale production to yield solid brominating reagent which is finally ground to get a homogeneous mixture of salts having bromine content in the range of 35–70%.

Yet another embodiment of the invention, wherein the said brominating are used to brominate aromatic compounds selected from group comprising bisphenal A, bromophenol, olefins such as styrene, cyclohexene and other class of compounds by activating in situ by the addition of stochiometric quantities of suitable mineral acid and preferably hydrochloric acid.

The following examples are given by way of illustrations and therefore should not be construed to limit the scope of the present invention.

EXAMPLE 1

To 9.2 ml of alkaline bromine solution containing 3.03 M $Br^-$ and 0.64 M $BrO_3^-$, 1.25 mmol (0.129 g) solid NaBr was added to obtain a 5:1 ratio of $Br^-$:$BrO_3^-$. The active bromine content in the mixture was >99%.

EXAMPLE 2

To 1.818 g (17.456 mmol) of styrene dissolved in 5 ml of dichloromethane in 250 ml round bottom flask, 5 ml of 12 N hydrochloric acid and 10 ml of water were added. A mixture of (3.035 g, 29.47 mmol) NaBr and 0.879 g (5.819 mmol) of $NaBrO_3$ dissolved in 20 ml water was added under stirring at room temperature over a period of 90 min. The organic layer was evaporated to get 39.3% of styrene dibromide, 60.6% styrene epoxide and 0.01% benzaldehyde.

EXAMPLE 3

0.909 g (8.73 mmol) of styrene dissolved in 5 ml of dichloromethane in 250 ml was taken in a round bottom flask fitted with a dropping funnel. In to the dropping funnel, 20 ml of 1.8 M hydrochloric acid and 20 ml of an aqueous solution containing 1.517 g (14.73 mmol) NaBr and 0.439 g (2.91 mmoles) of $NaBrO_3$ were added simultaneously at the same flow rate over a period of 30 mins and passage through the dropping finnel outlet insured uniform mixing of the solutions to generate $Br_2$ transiently, as per the reaction of equation 4, before falling into the stirred round bottom flask containing dissolved styrene at room temperature. After completion of addition, stirring was continued for an additional 15 min. The organic layer was then separated and evaporated and the crude solid dissolved in 25 ml methanol at room temperature. 25 ml of water was then added into the methanol and fine white solid separated. The solid which weighed 1.258 g after filtration and drying, was identified as styrene dibromide (mp 68–70° C.) with isolated yield of 54.6%.

EXAMPLE 4

5.0 g (21.93 mmol) of bisphenol-A, 50 ml of methanol and 18.4 ml of 12 N HCl were taken in a round bottom flask. 15.75 g NaBr (152.9 mmol) and 4.64 g (30.73 mmol) $NaBrO_3^-$ (were dissolved in 50 ml water and the solution added gradually into the flask over 1.5 h under stirring at room temperature. After completion of the reaction the white crystals that formed at the bottom were filtered and dried to yield 10.68 g (89.5%) of tetrabromobisphenol-A (mp 180° C.). The bromine atom efficiency with respect to desired product was 42.8%.

EXAMPLE 5

62.08 g of sodium hypochlorite was added to the alkaline bromine mixture containing 261.7 g dissolved bromine in sodium hydroxide. The contents were mixed thoroughly and allowed to react for 24 h in a closed 5 L round bottom flask to give brominating reagent containing 241.85 g (92.4%) of active bromine in solution form.

EXAMPLE 6

0.8 g of sodium hypochlorite was added to the alkaline bromine mixture containing 3.542 g of dissolved bromine in sodium hydroxide. The contents were mixed thoroughly and allowed to react for 12 h in a closed 250 ml round bottom flask. The reaction mixture was evaporated completely on a steam bath. The residue was dried under vacuum to give 9.65 g of solid brominating reagent containing 3.317 g (93.6%) active bromine.

EXAMPLE 7

12.77 g (0.085 moles) of sodium bromate dissolved in 50 ml of water was added to the alkaline bromine mixture containing 28.54 g of dissolved bromine in sodium hydroxide. The contents were mixed thoroughly for 30 min in a one L flask. The resulting solution was evaporated on a steam bath and dried under vacuum to give 67 g of solid brominating reagent containing 35.095 g (99.4%) of active bromine.

EXAMPLE 8

1 g (4.386 mmol) of bisphenol-A, 4.075 g of the brominating agent of Example 6 dissolved in 14.5 ml water (containing 17.511 mmol of reactive bromine) and 5 ml of dichloromethane were taken in a round bottom flask and a solution of 12 ml of 2 N hydrochloric acid was added over a period of 40 min under stirring at room temperature. Stirring was continued for another 30 min. 1.55 g of fine crystals were obtained on filtration and a further 0.67 g was obtained after evaporation of the organic layer to give a total product amount of 2.22 g (93.2%) tetrabromobisphenol-A (mp 176–182° C.) characterized by spectroscopic techniques. The bromine atom efficiency based on desired product and active bromine content was 93.2%.

EXAMPLE 9

4.3 ml of alkaline (lime) bromine (containing 0.242 g bromide and 0.051 g bromate per ml of solution) and 0.52 g sodium bromate in 10 ml water were taken in a round bottom flask with total bromine content of 19.135 mmol. Into this was added 2.5 g (18.517 mmol) of acetanilide in 12.5 ml dichloromethane. 25 ml of 3.6 N hydrochloric acid was added over a period of 13 min under stirring at room temperature. Stirring was continued for another 30 min. The precipitate was filtered, washed with water and dried to give 3.689 g (92.7%) of p-bromoacetanilide (m.p. 164–168° C.) characterized through spectroscopic techniques.

EXAMPLE 10

To 2.5 gm (26.596 mmoles) of phenol dissolved in a mixture of 30 ml water and 9 ml of 12 N hydrochloric acid, 18.568 g of the brominating agent of Example 6 (containing 79.788 mmol of reactive bromine) dissolved in 66 ml water was added over a period of 60 min under stirring at room temperature. Stirring was continued for another 30 min. The precipitate was filtered, washed with water and dried to give 8.495 g (96.5%) of tribromophenol (mp 84–89° C.) which was characterized through spectroscopic techniques.

EXAMPLE 11

1 g (7.407 mmol) of acetanilide, 1.724 g of the brominating agent of Example 6 dissolved in 6.2 ml water (containing 7.408 mmol of reactive bromine) and 5 ml of dichloromethane were taken in a round bottom flask and a a solution of 12 ml of 2 N hydrochloric acid was added over a period of 15 min under stirring at room temperature. Stirring was continued for another 30 min. The precipitate was filtered, washed with water and dried to give 1.402 g (88%) of p-bromoacetanilide (m.p. 164–168° C.) characterized through spectroscopic techniques.

The Main Advantages of the Present Invention Are:
(i) Inexpensive method of preparation of non-hazardous brominating reagents that are stable under storage and can be formulated either in solution or solid forms.
(ii) The brominating reagents can be prepared as a mixture of alkali bromide and bromate salts by utilizing the aqueous alkaline bromine mixture produced as intermediate in bromine recovery plants based on the Cold Process.
(iii) The alkaline bromine mixture with 5:1 bromide:bromate is a substitute for liquid bromine in bromine addition reactions and can be used for aromatic bromination reactions.
(iv) The brominating reagent with 2:1 bromide:bromate can be prepared from the alkaline bromine mixture through oxidation with inexpensive oxidizing agents and is especially suitable for aromatic bromine reactions with high Br atom efficiency that avoids the formation of HBr.
(v) The brominating reagents are activated by simple addition of mineral acid and no catalyst is required for the bromination reactions.
(vi) Bromination reaction can be carried out with the present brominating reagents under ambient conditions.

What is claimed is:

1. A process for the preparation of a non hazardous brominating reagent wherein an aqueous alkaline bromine solution obtained from a bromine recovery plant is treated with either (a) an alkali bromide or (b) an oxidizing agent to obtain a stoichiometric ratio of bromide to bromate in the range 5.1:1 to 2:1 in said aqueous alkaline bromine solution and wherein the treated solution has a pH in the range of 8.0 to 12.

2. A process for the preparation of a non hazardous brominating reagent wherein an aqueous alkaline bromine solution obtained from a bromine recovery plant comprising 25 to 35% of bromine dissolved in aqueous lime or sodium hydroxide as alkali bromide and alkali bromate and having a pH in the range of 8.0 to 12.0 is treated with either (a) an alkali bromide to obtain a stoichiometric ratio of bromide to bromate in the range 5.1:1 to 5:1 or (b) with an oxidizing agent to obtain a stoichiometric ratio of bromide to bromate in the range 2.1:1 to 2:1 and wherein the treated solution has a pH in the range of 8.5 to 10.5 and contains 100–350 g/L of bromine.

3. The process as claimed in claim 2 wherein water is evaporated from the brominating reagent to form a solid comprising 45 to 55% w/w of bromine.

4. A process as claimed in claim 2 wherein the bromide to bromate ratio of 5.1:1 to 5:1 is obtained by adding an appropriate quantity of alkali bromide salt to the aqueous alkaline bromine solution.

5. The process as claimed in 2 the bromide to bromate ratio of 2.1:1 to 2:1 is achieved by treating the aqueous alkaline bromine solution with 1–10% concentration of aqueous sodium hypochloride for a period of 6–24 hours at a temperature in the range of 25–30° C.

6. The process as claimed in claim 2 wherein the bromide to bromate ratio of 2.1:1 to 2:1 is achieved by adding alkali into the aqueous alkaline bromine solution followed by passing chlorine gas through said solution to generate hypochloride in situ which oxidizes the bromide salt to the bromate salt.

7. The process as claimed in claim 2 Wherein the bromide to bromate ratio of 2.1:1 to 2:1 of the alkaline bromine solution is decreased by adding appropriate quantity of alkaline bromate salt.

8. The process as claimed in claim 7 wherein the alkaline bromate salt is a sodium or calcium bromate and wherein the salt is added such that the pH of the solution remains between 8–10 and there is no rise in temperature.

9. The process as claimed in claim 2 wherein the water is evaporated from the brominating reagent by employing solar pans for large scale production to obtain a solid brominating reagent which is finally ground to obtain a homogenous mixture of salts having a bromine content in the range of 90–100%.

10. A method of brominating aromatic compounds wherein said aromatic compounds are contacted with a brominating reagent as claimed in claim 1.

11. The method as claimed in claim 10 wherein the brominating reagent is activated in situ during the bromination reaction through the addition of a stoichiometric quantity of a mineral acid.

12. The method as claimed in claim 11 wherein the mineral acid is hydrochloric acid.

13. The method as claimed in claim 12 wherein the aromatic compound is selected from the group consisting of bisphenol A, bromophenol and styrene.

* * * * *

UNITED STATES PATENT AND TRADEMARK OFFICE
CERTIFICATE OF CORRECTION

PATENT NO. : 6,740,253 B2  Page 1 of 1
DATED : May 25, 2004
INVENTOR(S) : Ramachandraiah Gaade et al.

It is certified that error appears in the above-identified patent and that said Letters Patent is hereby corrected as shown below:

Title page,
Item [75], Inventors, "Rajinder ... Sanghavi," should read -- Gadde Ramchandraiah, Ghosh Pushpito Kumar, Mehta Aditya Shantibhai, Subbarayappa Adimurthy, Jethava Ashok Dayabhai, Vaghela Sanjay Shambhubhai, all of --.

Signed and Sealed this

Thirty-first Day of August, 2004

JON W. DUDAS
*Director of the United States Patent and Trademark Office*